(12) United States Patent
Ahearn et al.

(10) Patent No.: US 10,874,294 B2
(45) Date of Patent: Dec. 29, 2020

(54) TRACK LIGHTING SYSTEM

(71) Applicant: David J. Ahearn, Little Compton, RI (US)

(72) Inventors: David J. Ahearn, Little Compton, RI (US); Edward Carey, Westport, MA (US)

( * ) Notice: Subject to any disclaimer, the term of this patent is extended or adjusted under 35 U.S.C. 154(b) by 0 days.

(21) Appl. No.: 15/891,996

(22) Filed: Feb. 8, 2018

(65) Prior Publication Data

US 2018/0160891 A1 Jun. 14, 2018

Related U.S. Application Data

(63) Continuation-in-part of application No. 14/873,308, filed on Oct. 2, 2015, now abandoned, which is a
(Continued)

(51) Int. Cl.
| | |
|---|---|
| *F21S 8/06* | (2006.01) |
| *A61C 19/00* | (2006.01) |
| *A61B 90/30* | (2016.01) |
| *F21W 131/202* | (2006.01) |
| *F21V 21/28* | (2006.01) |
| *A61B 90/00* | (2016.01) |
| *F21Y 115/10* | (2016.01) |

(Continued)

(52) U.S. Cl.
CPC .......... *A61B 1/247* (2013.01); *A61B 1/00128* (2013.01); *A61B 90/30* (2016.02); *A61C 19/00* (2013.01); *F21S 8/066* (2013.01); *A61B 2090/309* (2016.02); *A61B 2090/372* (2016.02); *F21S 8/06* (2013.01); *F21V 21/28* (2013.01); *F21W 2131/202* (2013.01); *F21Y 2115/10* (2016.08)

(58) Field of Classification Search
CPC ..... A61B 1/247; A21C 2203/00; F21V 21/34; F21V 21/35; F21V 21/403; F21W 2131/202; H01R 25/142
USPC .................................................. 362/573, 648
See application file for complete search history.

(56) References Cited

U.S. PATENT DOCUMENTS

| 1,381,807 A | * | 6/1921 | Daffron | ..................... B60L 5/06 |
| | | | | 191/60.4 |
| 4,712,165 A | * | 12/1987 | Cetrone | .................... F21S 2/00 |
| | | | | 362/147 |

(Continued)

*Primary Examiner* — Leah Simone Macchiarolo
(74) *Attorney, Agent, or Firm* — Adler Pollock & Sheehan P.C.

(57) ABSTRACT

A system includes a housing assembly having a top, side, middle, and bottom portions, a pair of hollow, tubular, elongated members having a top and a bottom end, the top portion of the housing assembly attached to the bottom end of the elongated members, the top end of the one or more elongated members having a brackets configured and arranged to mount to an overhead surface area, one or more ambient lighting assemblies attached to side portions and top portion of the housing assembly to provide general lighting, each ambient lighting assembly including an ambient housing and fluorescent bulbs, a horizontal tracking rail suspended attached to a bottom portion of the housing assembly, the tracking rail extending along a portion of the housing assembly, a carriage mechanism slidably engaging the tracking rail, and an intra-oral light assembly connected to the carriage mechanism.

8 Claims, 19 Drawing Sheets

Related U.S. Application Data continuation of application No. 13/309,529, filed on Dec. 1, 2011, now Pat. No. 9,149,350.

(60) Provisional application No. 61/418,427, filed on Dec. 1, 2010.

(51) Int. Cl.
*A61B 1/247* (2006.01)
*A61B 1/00* (2006.01)

(56) References Cited

U.S. PATENT DOCUMENTS

| | | | | |
|---|---|---|---|---|
| 5,025,355 A * | 6/1991 | Harwood | ............... | F21S 8/06 |
| | | | | 362/147 |
| 5,455,754 A * | 10/1995 | Hoffner | ............... | F21V 21/35 |
| | | | | 362/147 |
| 6,290,368 B1 * | 9/2001 | Lehrer | ............... | F21L 4/06 |
| | | | | 362/103 |
| 6,638,088 B1 * | 10/2003 | Richardson | ............ | F21V 19/008 |
| | | | | 439/242 |
| 2003/0053311 A1 * | 3/2003 | Wahl | ............... | F21V 21/34 |
| | | | | 362/233 |
| 2004/0178312 A1 * | 9/2004 | Parsons | ............... | A61G 15/10 |
| | | | | 248/276.1 |

* cited by examiner

TRACK LIGHTING SYSTEM

CROSS REFERENCE TO RELATED APPLICATIONS

This application is a Continuation-in-Part of U.S. patent application Ser. No. 14/873,308, filed Oct. 2, 2015, which is a Continuation of U.S. patent application Ser. No. 13/309,529, filed Dec. 1, 2011, now U.S. Pat. No. 9,149,350, which claims benefit from U.S. Provisional Patent Application Ser. No. 61/418,427, filed Dec. 1, 2010, each of which are incorporated herein by reference in their entireties.

BACKGROUND OF THE INVENTION

The invention generally relates to track mounted lighting. In particular, the invention is directed towards a pendant mounted track lighting system that incorporates and integrates intraoral illumination for illuminating a patient's oral cavity, general room or ambient lighting in the operatory environment for patients and practitioners, directional task lighting for work surface areas, and electronic display for patient stimulation all in a single track lighting system.

It is often necessary to move a light source such as an electric light within a room or other space to provide lighting where it is most needed. One response to this desire for portability is found in track lighting, which is found in many residential and commercial uses.

Similarly, in operating rooms, it is frequently desired to move a light source to a specific location dictated by the positioning of the surgical apparatus, location of the practitioner, and the location of the patient. Numerous apparatus for allowing lighting fixtures to be moved about the room have been designed in response to this need. Among them is a longitudinal track running along at least a portion of the ceiling of the operating room and a carriage mechanism for engaging the track an allowing the light assembly to slide along it.

Track mounted lighting systems are found in various health care examination and treatment facilities, such as medical and dental operations. For example, U.S. Pat. No. 3,936,671 discloses an illumination system, particularly adapted to use in hospitals, has an elongated, low-profile fluorescent lighting fixture on the side of and parallel to a track, a reading-examination light mounted on one end of a telescoping boom, the other end of which is swingably connected to a boom mount rotatably carried by a carriage mounted to roll along the track.

The lighting fixture of the '671 patent includes means for providing low brightness down lighting and higher brightness side lighting. The reading-examination light is so constructed as to permit two levels of illumination from a single light source and color correction in a small, balanced, easily manipulated unit. The telescoping boom and its mounting are so constructed as to be light, strong and stable in any position within wide limits. The carriage is so constructed as to permit easy transport of the boom and light, and positive and continuous connection of electrical conductors within the boom to a source of current.

Numerous single solution products exist for track mounted intraoral lighting made by companies such as Adec, Pelton, Crane & Marus. However, these lighting products are only single solution products, designed solely for exam lighting of an oral cavity of a patient. A small number of companies may even add a second feature, such as a carriage mechanism, to these single solution products.

Therefore, it would be particularly desirable to provide a track lighting system that would incorporate or integrate track mounted intraoral illumination, general room or ambient lighting, task lighting, and electronic display into a single track lighting system.

BRIEF SUMMARY OF THE INVENTION

An embodiment of the invention preserves the advantages of prior art track lighting systems. In addition, it provides new advantages not found in currently available track lighting systems and overcomes many disadvantages of such currently available track lighting systems.

The invention is a pendant mounted track lighting system having an electronic display for use in an operatory environment, specifically a dental operatory environment. In particular, the invention is directed towards a pendant mounted track lighting system that incorporates and integrates intraoral illumination for illuminating a patient's oral cavity, general room or ambient lighting in the operatory environment for patients and practitioners, directional task lighting for work surface areas, and electronic display for patient stimulation.

The track lighting system includes a housing assembly attached to one or more elongated members for attachment within the operatory environment, one or more ambient lighting assemblies, an intraoral light assembly having a carriage mechanism, an electronic display, and one or more directional task lighting assemblies in a single track lighting system. In one embodiment, the tracking lighting system further includes an operatory chair include a head rest attached to a floor area of the operatory environment. A power source (not shown) is connected to the track lighting system and the electronic display to operate the lighting options and the electronic display.

The housing assembly includes a top, side, and bottom portions and is configured for providing multiple lighting options and an electronic display. The top portion of the housing assembly provides a top surface area for concealing wiring, cabling, junction boxes and other components for the track lighting system.

The one or more elongated members have a top and a bottom end. In one embodiment, the elongated members may defined a cylindrical or tubular shape with a hallowed interior for concealing wires, cables, and other components of the track lighting system. The top portion of the housing assembly is attached to the bottom end of the one or more of the elongated members. The bottom end of the one or more elongated members may be attached to the housing assembly above the head rest of the operatory chair in the operatory environment.

The top end of the one or more elongated members is mounted to a first surface area within the operatory environment. In one embodiment, the first surface area within the operatory environment is a ceiling area. The bottom end of one or more elongate members is located within a first predetermined distance from a second surface area within the operatory environment. For example, the first predetermined distance from the bottom end of the one or more elongated members to a floor area is approximately less than ten feet. Alternatively, the first predetermined distance is approximately seven and a half feet. Of course, the first predetermined distance may be adjusted depending upon the height of the ceiling in the operatory environment and the height of the head rest of the operatory chair above the floor area. In one embodiment, the second surface area within the operatory environment is a floor area or, alternatively, the head rest of the operatory chair.

The one or more ambient lighting assemblies are attached to one or more side portions and the top portion of the housing assembly to provide general lighting in the operatory environment for practitioners and patients.

The intraoral light assembly is used for illuminating a patient's mouth area, specifically oral cavity. The intraoral light assembly includes an intraoral lamp and an articulating arm for pivotal, horizontal, and vertical movement relative to the operatory chair. The intraoral light assembly is attached to a carriage mechanism for slidably engaging a tracking rail attached to the bottom portion of the housing assembly along a horizontal axis for translational movement thereof. The distance between the intraoral light assembly relative to the operatory chair is variable depending upon the practitioner's needs.

The electronic display is used for a patient's visual and audio stimulation during treatment in the operatory environment. The electronic display is fixedly attached to a bottom portion of the housing assembly. The electronic display is mounted along a horizontal axis parallel to the housing assembly and within a second predetermined distance from the second surface area within the operatory environment. In one embodiment, the second predetermined distance is approximately less than seven and a half feet. Alternatively, the second predetermined distance is approximately four and a half feet. Of course, the second predetermined distance may be adjusted depending upon the height of the ceiling in the operatory environment and the height of the head rest of the operatory chair above the floor area. It should be noted that the second predetermined distance may be less than the first predetermined distance.

The one or more directional task lighting assemblies is attached to a bottom portion of the housing assembly to provide lighting to work surface areas used by a practitioner in the operatory environment. The one or more directional task lighting assemblies includes one or more directional LEDs or other light producing members or elements to provide light to specific surface areas in the operatory environment. The one or more directional task lighting assemblies, in one embodiment, includes three directional LEDS to provide light to surrounding work surface areas in the operatory environment. In one embodiment, the task lighting assembly is located proximal to the electronic display. In operation, the track lighting system and the electronic display is more easily controlled by the practitioner in the operatory environment since all of the lighting options and electronic display are convenient to the practitioner in a single track lighting system which is important, especially during an operation.

It is therefore an object of the invention to provide a single track lighting system that incorporates and integrates intraoral illumination, ambient lighting, task lighting, and an electronic display.

It is a further object of the present invention is to improve the practitioner's ability to manipulate his lighting options and electronic display using a single track lighting system.

It is also an object of the present invention to provide enhanced lighting options in the operatory environment to improve the performance and efficiency of the practitioner by allowing the intraoral lamp assembly to move independent of the electronic display.

Another object of the present invention is to minimize the usage of space in the operatory environment by using a single track lighting system.

Furthermore, another object of the present is to provide electronic display respectively above a patient's head at a fixed position to prevent the practitioner from needlessly bumping into or constantly adjusting the electronic display.

Other objects, features and advantages of the invention shall become apparent as the description thereof proceeds when considered in connection with the accompanying illustrative drawings.

BRIEF DESCRIPTION OF THE DRAWINGS

The novel features which are characteristic of the track lighting system are set forth in the appended claims. However, the track lighting system, together with further embodiments and attendant advantages, will be best understood by reference to the following detailed description taken in connection with the accompanying drawings in which:

DETAILED DESCRIPTION OF PREFERRED EMBODIMENTS

In FIGS. 1-12, the pendant mounted track lighting system 10 with electronic display 12 for use in an operatory environment is shown. In particular, the invention is directed towards a pendant mounted track lighting system 10 that incorporates and integrates intraoral illumination for illuminating a patient's oral cavity, general room or ambient lighting in the operatory environment for patients and practitioners, directional task lighting for work surface areas, and electronic display, such as a television or computer monitor, for patient stimulation during treatment. The invention will provide the lighting options (intraoral illumination, ambient lighting, directional task lighting) and the electronic display in a single track lighting system to improve overall delivery of operatory services in the operatory environment and minimize the usage of space in the operatory environment which is at a premium.

It should be understood that this invention is well suited and preferably used in a dental office environment; however, it may be used in any environment where delivery of objects to a work area is desired. The invention will be disclosed herein in connection with a dental office environment; however, the present invention is not intended to be limited to that particular use.

Figure 1:
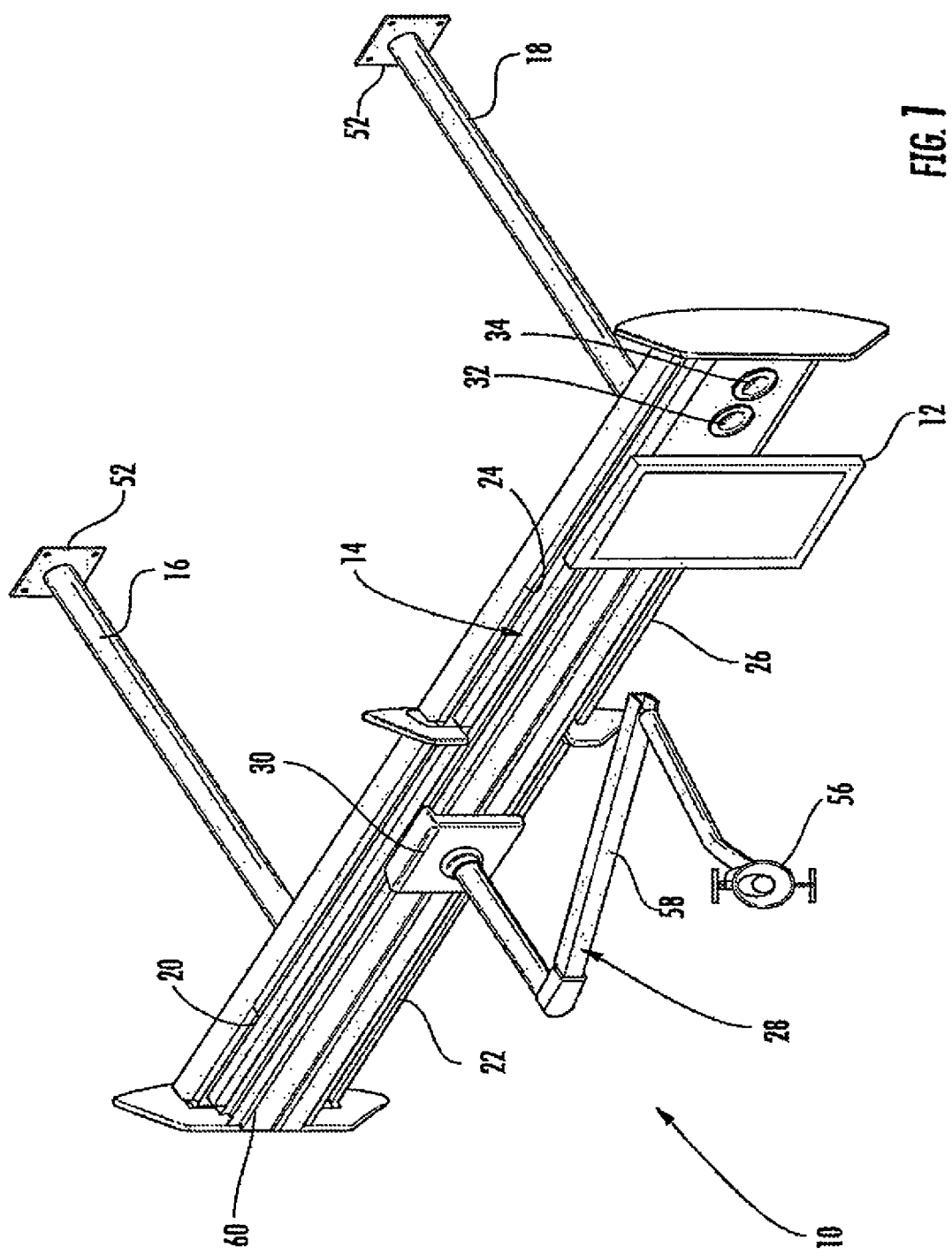
FIG. 1 is a perspective view of the track lighting system with electronic display.
Figure 12:
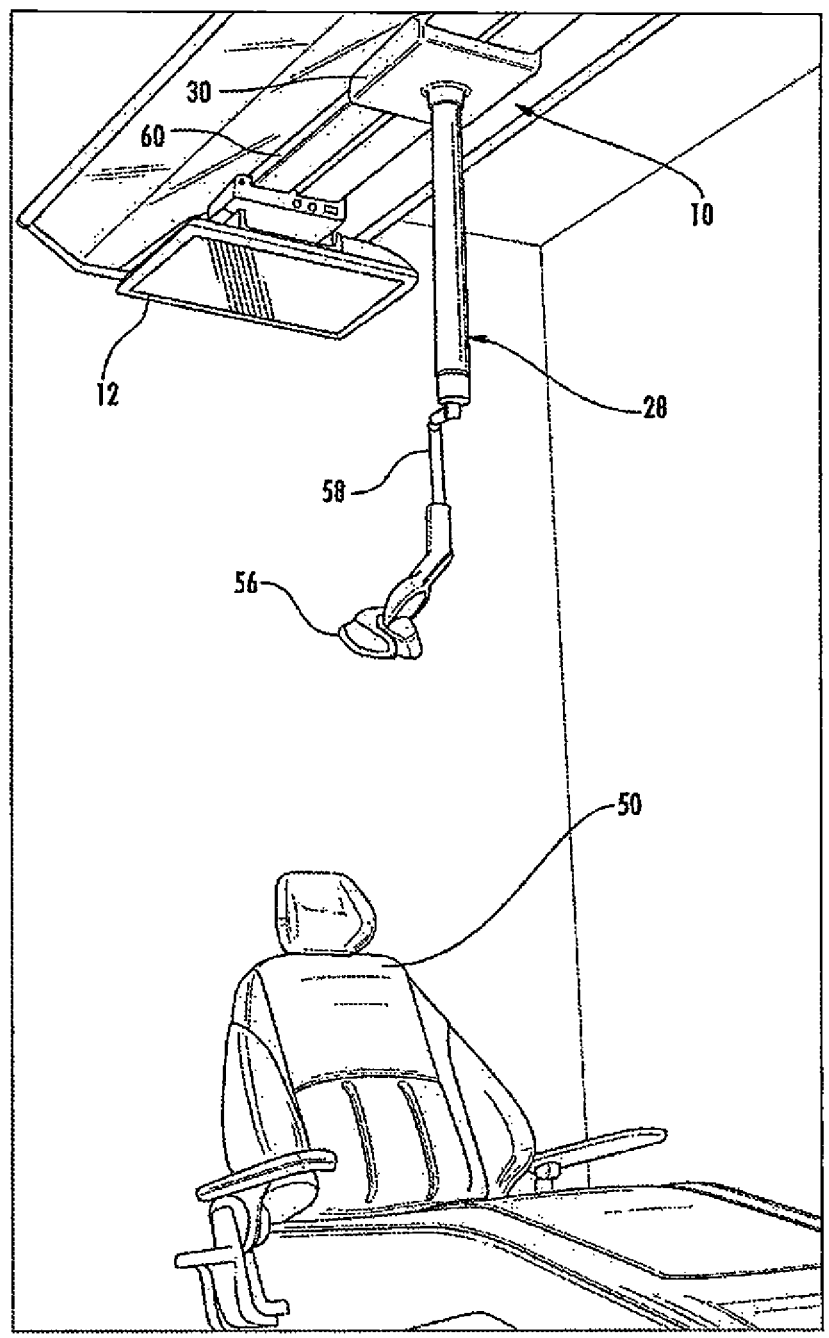
FIG. 12 is a partial bottom view of an embodiment of the track lighting system including in an operatory environment including an operatory chair.

Referring to FIG. 1, the track lighting system 10 includes a housing assembly 14 attached to one or more elongated members 16, 18 for attachment within the operatory environment, one or more ambient lighting assemblies 20,22, 24,26, an intraoral light assembly 28 having a carriage mechanism 30, the electronic display 12, and one or more directional task lighting assemblies 32, 34 in a single track lighting system. Referring to FIG. 12, in one embodiment, the tracking lighting system 10[[A]] further includes an operatory chair 50 including a head rest attached to a floor area of the operatory environment. A power source (not shown) is operationally connected to the track lighting system 10 and the electronic display 12 to operate the lighting options and the electronic display 12.

Figure 2:
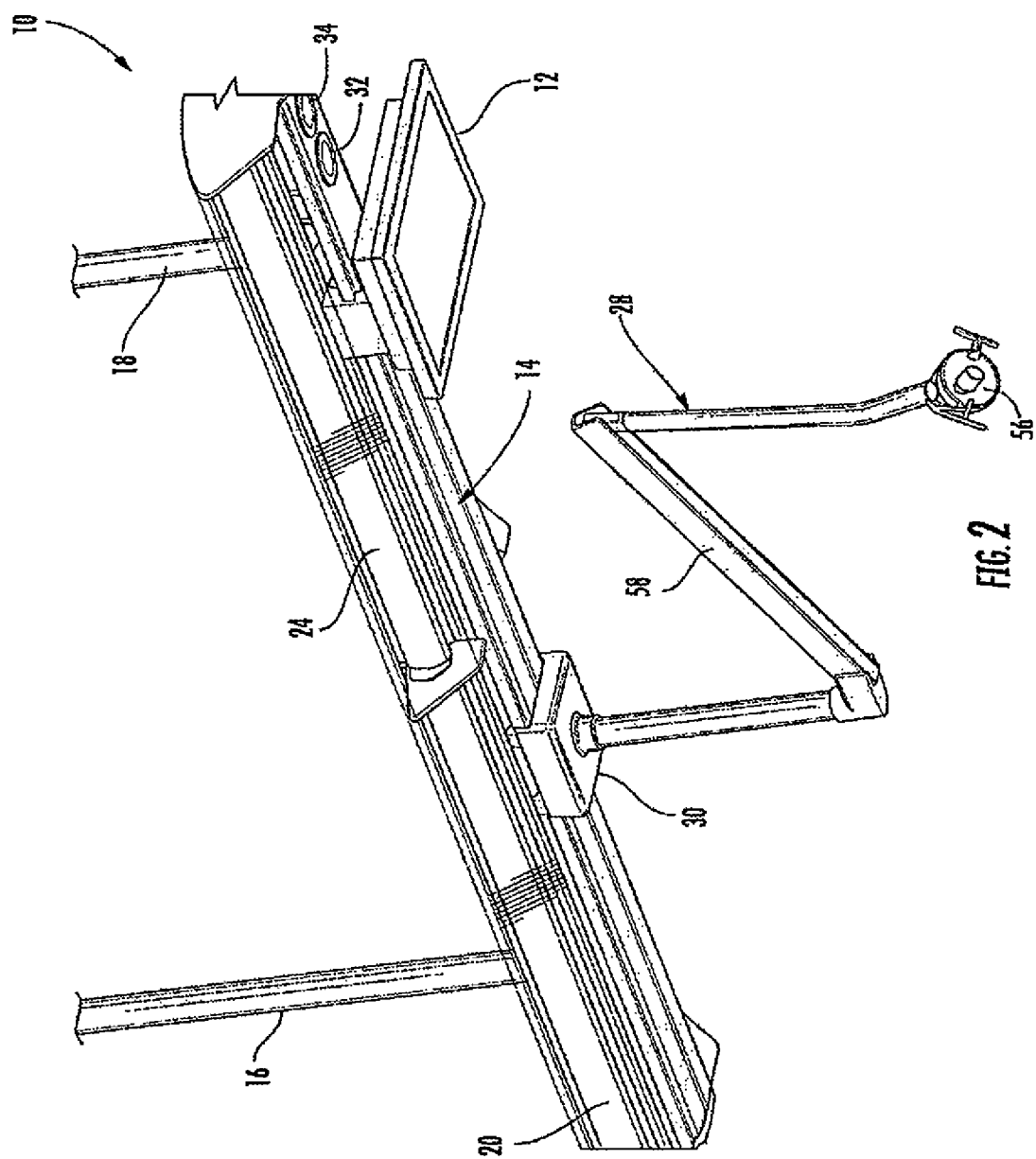
FIG. 2 is an elevated right side view of the invention of FIG. 1.

Referring to FIG. 2, the housing assembly 14 includes a top 36, side 38, middle 40, and bottom 42 portions and is configured for providing multiple lighting options and an electronic display 12. The top portion 36 of the housing assembly 14 provides a top surface area for concealing wiring, cabling, junction boxes and other components for the track lighting system 10. The middle portion 40 of the housing assembly 14 includes middle brackets 46 located between one or more ambient lighting assemblies 20, 22, 24, 26.

The one or more elongated members 16, 18 have a top and a bottom end. In one embodiment, the elongated members may define a cylindrical or tubular shape, such as a post. The elongated members 16, 18 may have a hallowed interior for concealing wires, cables, and other electrical or miscellaneous components of the track lighting system. The length of the elongated members 16, 18 may be adjusted to ensure proper mounting height of the track lighting system 10 which is important due to variable ceiling heights of operatory environments. In one embodiment, the elongated members 16, 18 may telescope to a desired height for the track lighting system 10. The top portion 36 of the housing assembly 14 is attached to the bottom end of the one or more of the elongated members 16, 18. The bottom end of the one or more elongated members 16, 18 may be attached to the housing assembly 14 above the head rest of the operatory chair 50 in the operatory environment.

Figure 6:
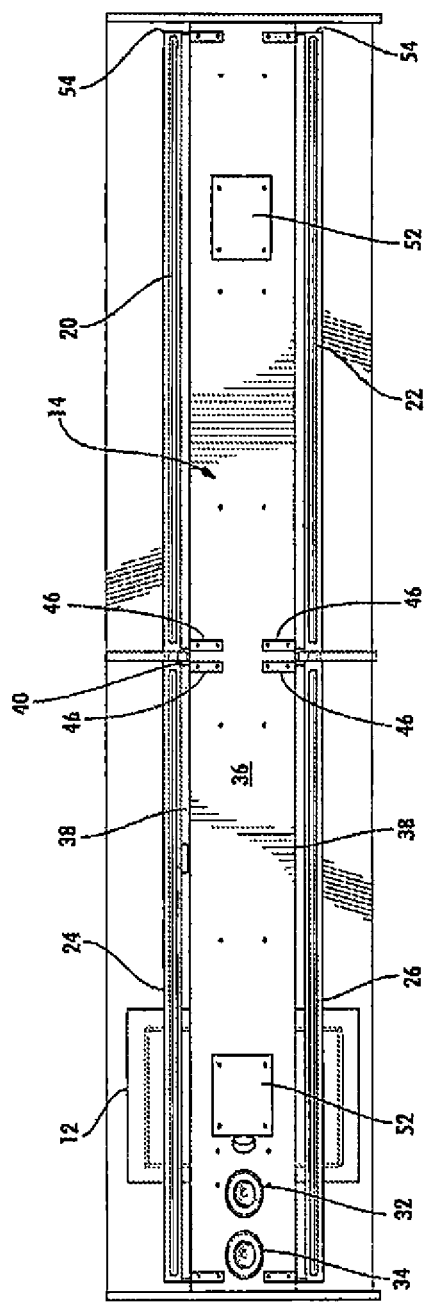
FIG. 6 is a top view of the invention of FIG. 1.

Referring to FIG. 6, the top end of the one or more elongated members 16, 18 is mounted to a first surface area within the operatory environment. In one embodiment, the first surface area within the operatory environment is a ceiling area. In one embodiment, the elongated members 16, 18 are pendant mounted to a ceiling area using brackets 52 generally defining a square or rectangular shape using fasteners. Furthermore, the elongated members 16, 18 may have a sufficient length to extend from the ceiling area and through a cut-out in a drop ceiling. Of course, the track lighting system 10 may be mounted by other means to provide multiple lighting options within an operatory environment of varying sizes.

Referring to FIG. 12, the bottom end of one or more elongate members 16, 18 is located within a first predetermined distance from a second surface area within the operatory environment. For example, the first predetermined distance from the bottom end of the one or more elongated members 16, 18 to a floor area is approximately less than ten feet. Alternatively, the first predetermined distance is approximately seven and a half feet. Of course, the first predetermined distance may be adjusted depending upon the height of the ceiling in the operatory environment and the height of the head rest of the operatory chair 50 above the floor area. In one embodiment, the second surface area within the operatory environment is a floor area or, alternatively, the head rest of the operatory chair 50.

Figure 3:
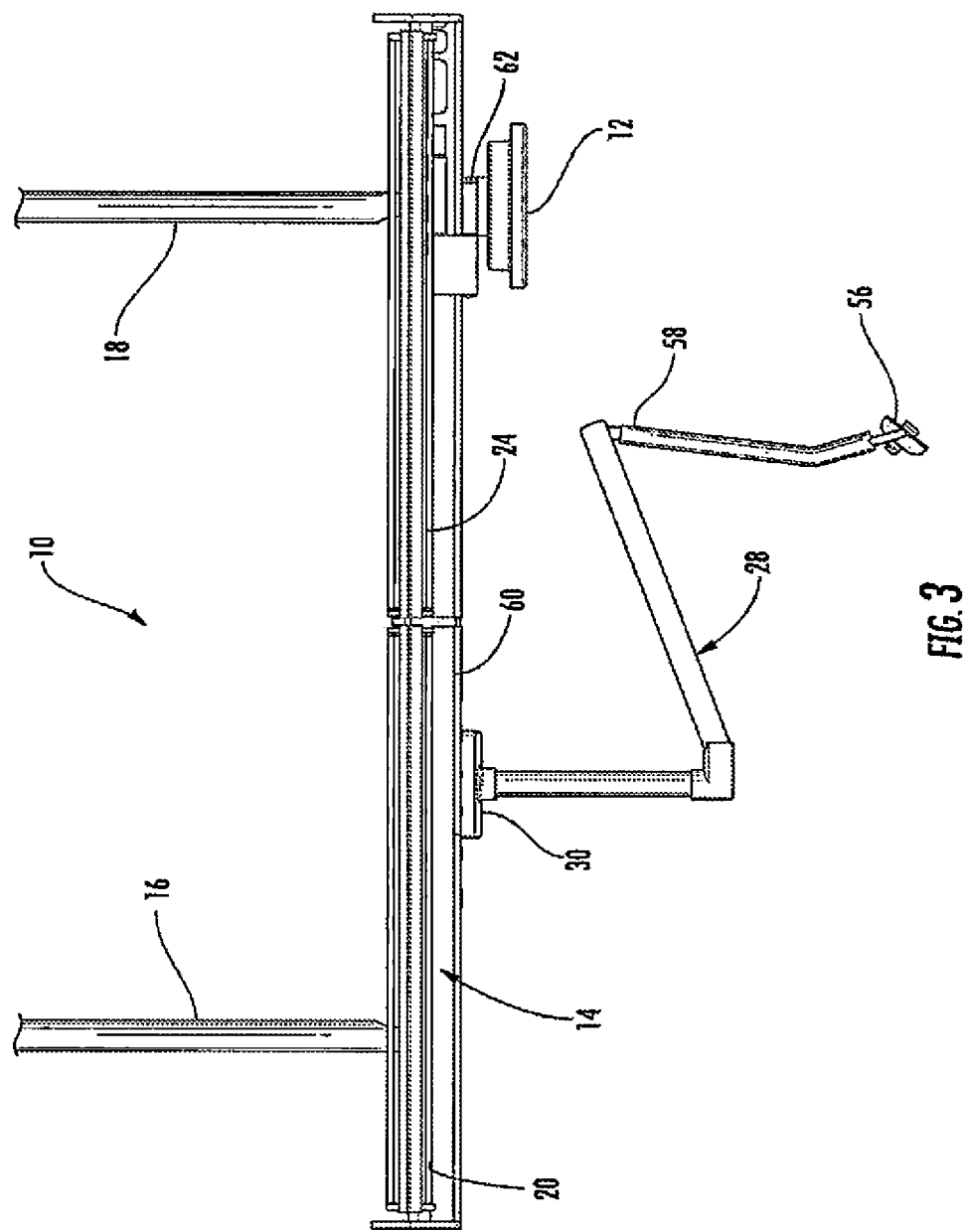
FIG. 3 is a side view of the invention of FIG. 1.
Figure 11:
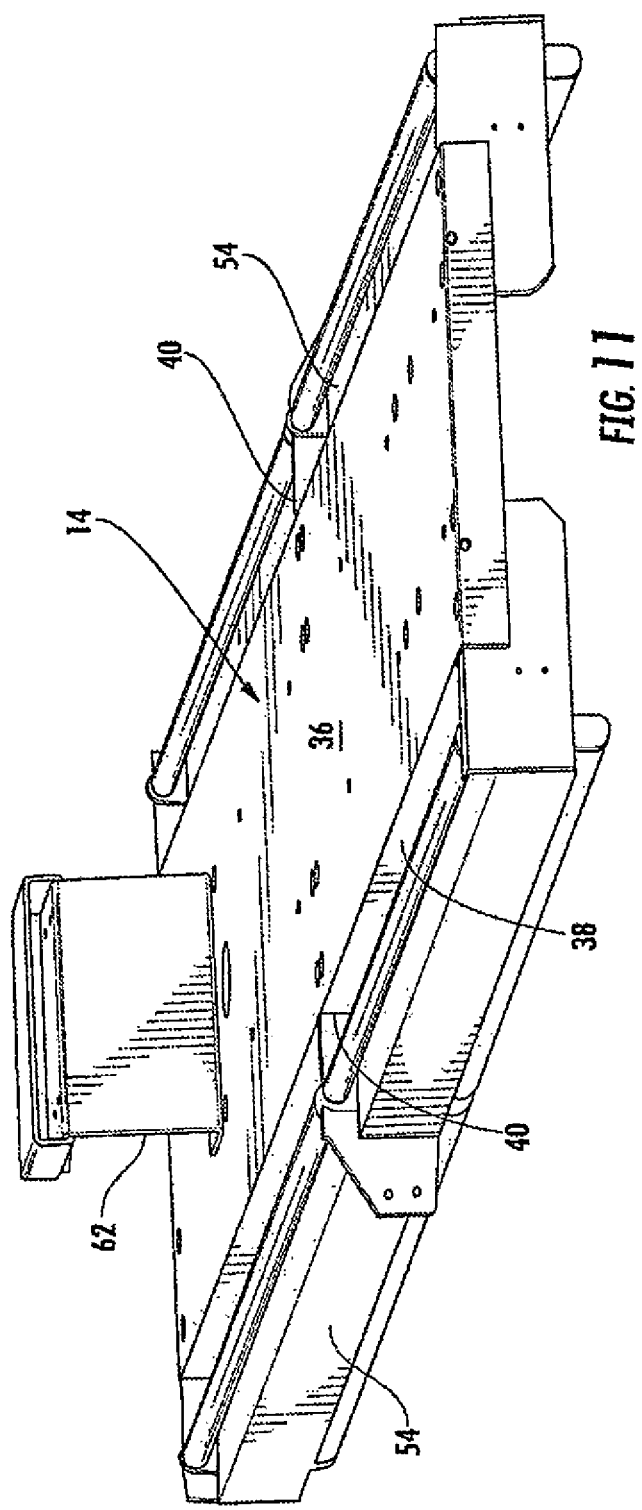
FIG. 11 is an isometric view of the housing assembly, ambient lighting assemblies, and the bracket for attaching the electronic display of FIG. 1.

Referring to FIG. 3 and FIG. 11, with regards to the general or ambient room lighting, the one or more ambient lighting assemblies 20, 22, 24, 26 are attached to one or more side portions 38 and the top portion 36 of the housing assembly 14 to provide general lighting in the operatory environment for practitioners and patients. Of course, the ambient lighting assemblies 22, 24, 26, 28 may also be attached to a side portion 38, top portion 36, or bottom portion 42 of the housing assembly 14 if so desired. In one embodiment, one or more ambient lighting assemblies 22, 24, 26, 28 may include an ambient housing 54 with one or more, preferably at least four, T5 HO fluorescent fixtures/bulbs to provide general ambient lighting.

Figure 4:
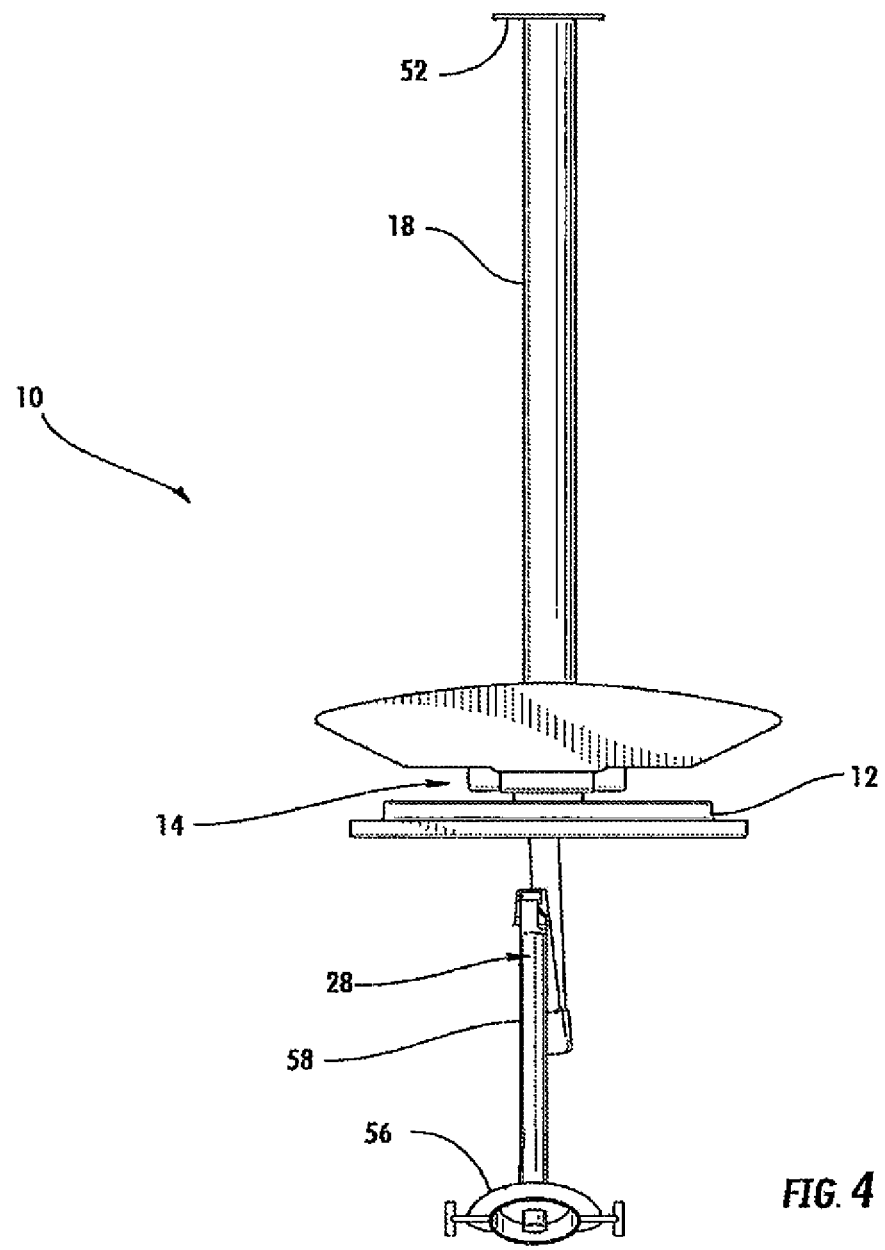
FIG. 4 is a front view of the invention of FIG. 1.
Figure 9:
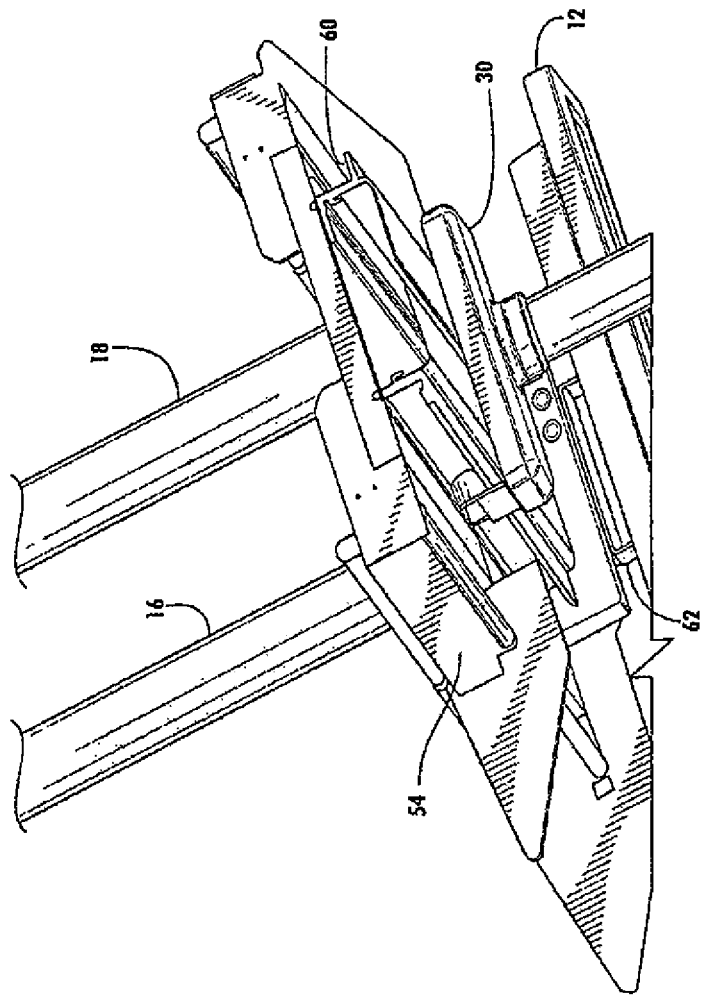
FIG. 9 is a sectional view of the invention of FIG. 1 showing detail of the carriage mechanism engaging the tracking rail.
Figure 10:
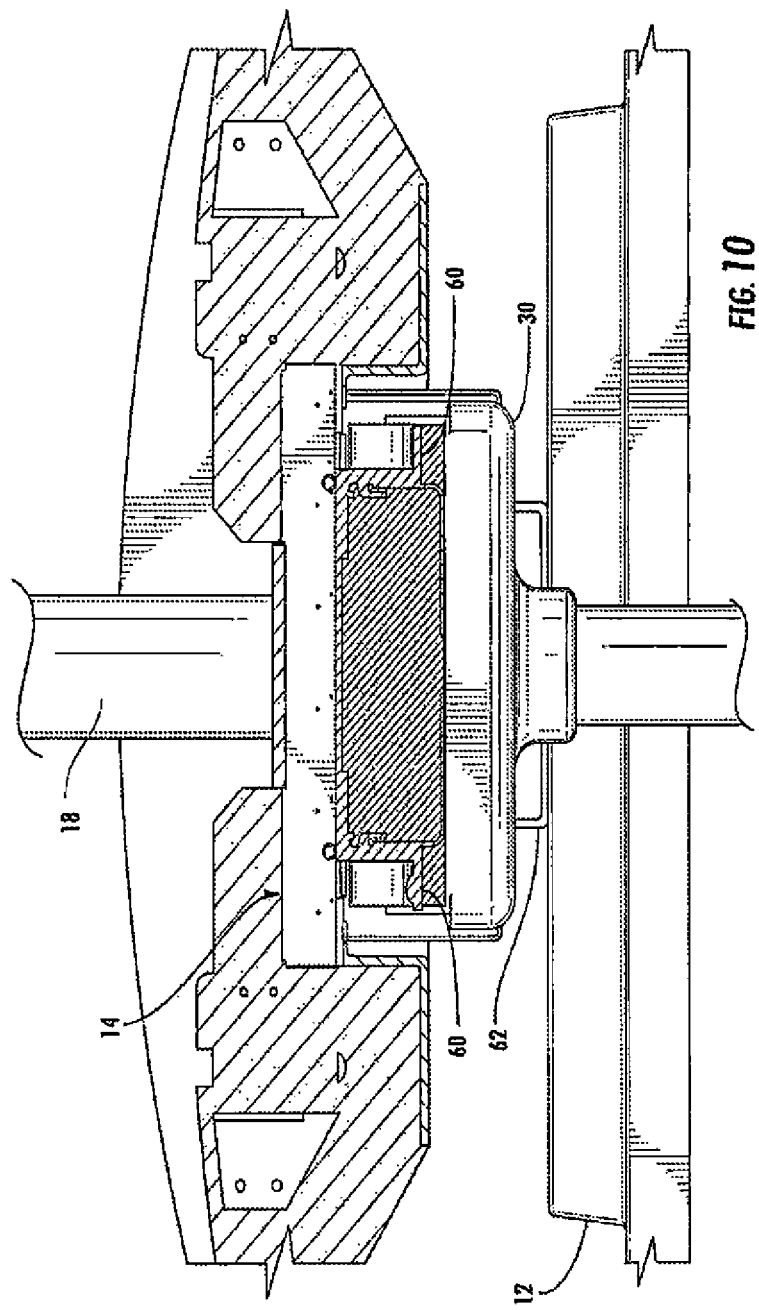
FIG. 10 is a front sectional view of the invention of FIG. 1 showing detail of the elongated member, carriage mechanism, and the housing assembly.

Referring to FIGS. 4 and 9-10, the intraoral illumination provides supplement lighting during an operatory procedure. More specifically, the intraoral light assembly 28 is used for illuminating a patient's mouth area, specifically oral cavity. The intraoral light assembly 28 includes an articulating intraoral lamp or light assembly 56 and articulating arm 58 configured for pivotal, horizontal, and vertical movement relative to the operatory chair 50. The intraoral light assembly 24 is attached to a carriage mechanism 30 for slidably engaging a horizontal tracking rail 60 attached to the bottom portion 42 of the housing assembly 14 along a horizontal axis for translational movement thereof. The tracking rail 60 runs along at least a portion of the track lighting system 14 and the carriage mechanism 30 is used for engaging the tracking rail 60 and the articulating arm 58 to allow the articulating intraoral lamp 56 to slide along it. The distance between the intraoral light assembly 28 relative to the operatory chair 50 is variable depending upon the practitioner's needs.

Figure 5:
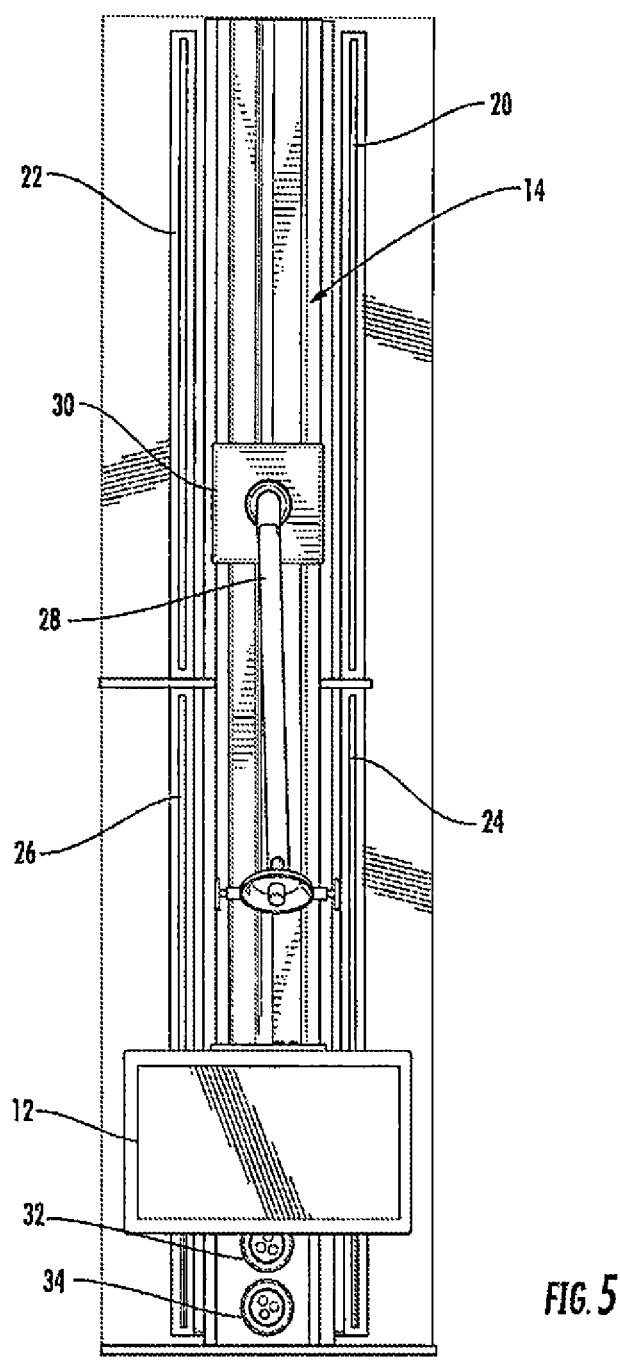
FIG. 5 is bottom view of the invention of FIG. 1.
Figure 7:
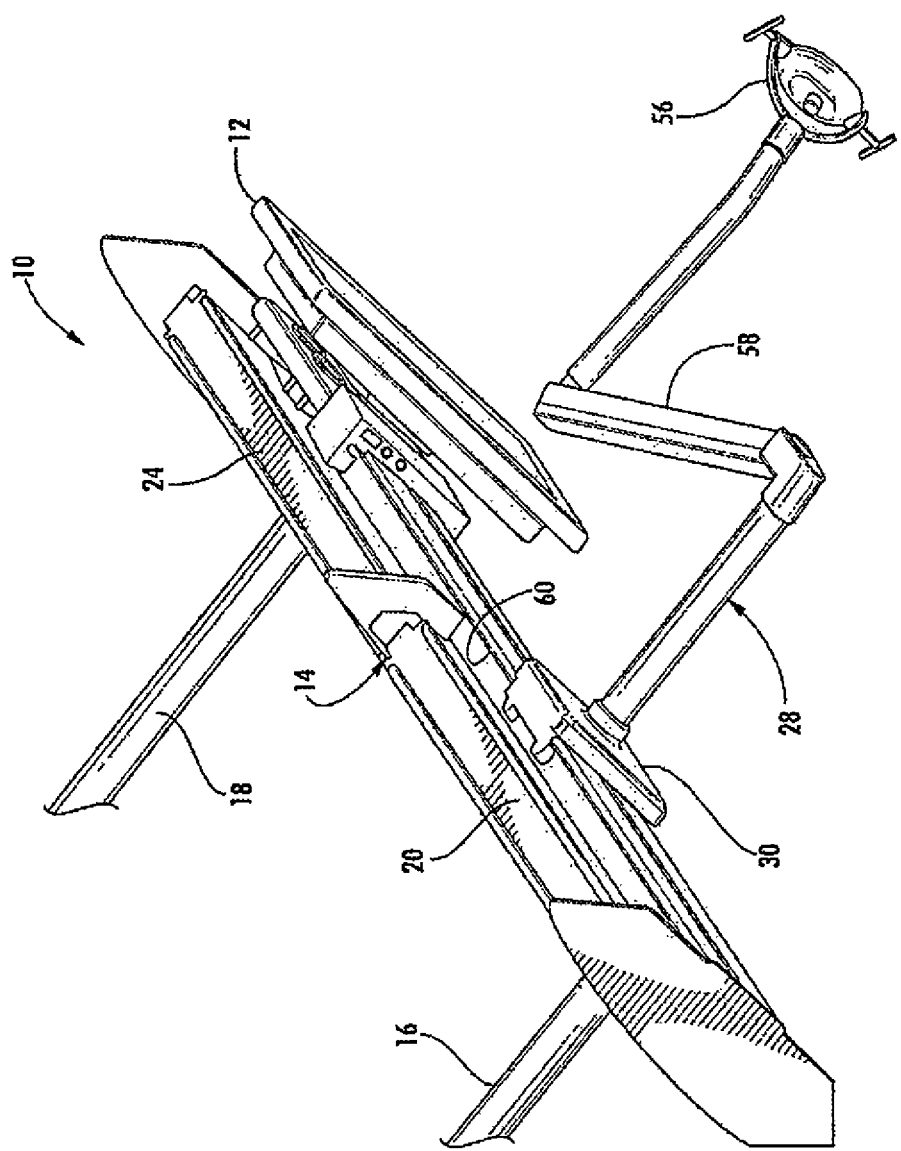
FIG. 7 is a rear view of the invention of FIG. 1.
Figure 8:
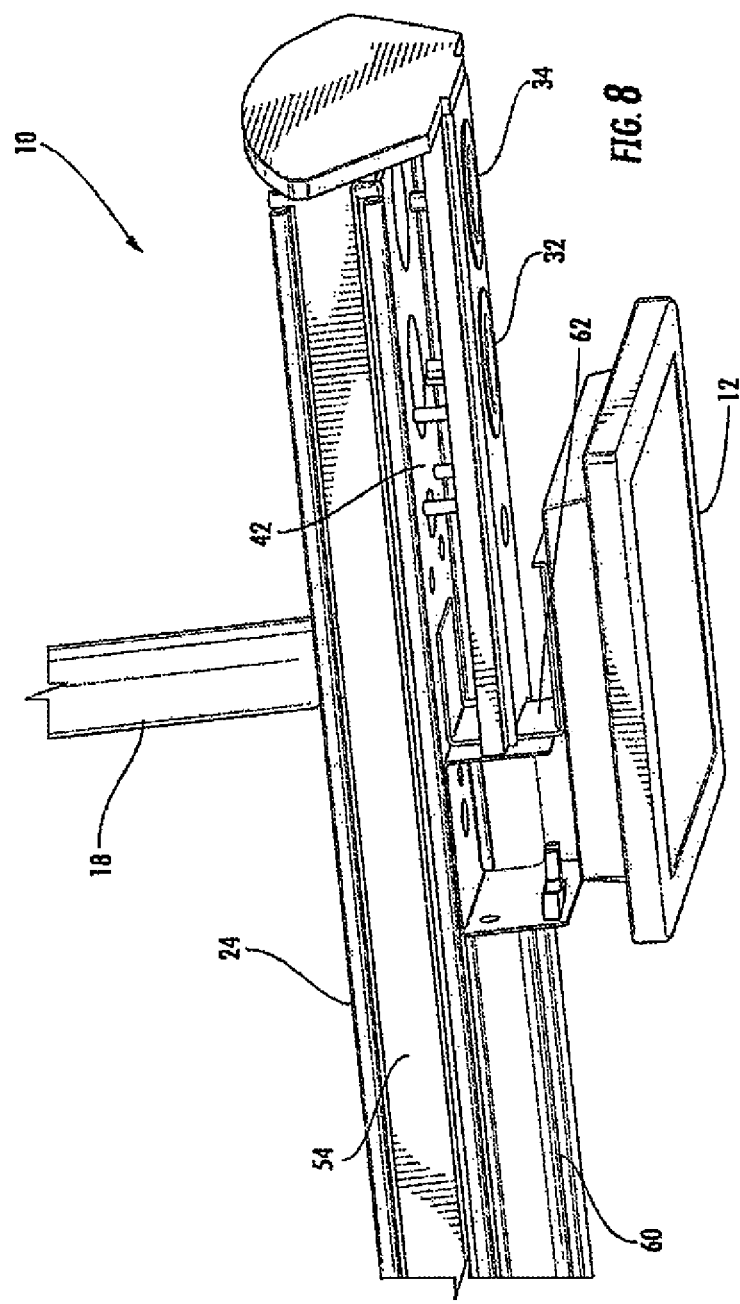
FIG. 8 is side view of the invention of FIG. 1 showing detail of the electronic display and the directional task lighting.

Referring to FIGS. 5 and 7-8, the electronic display 12 is used for a patient's visual and audio stimulation during treatment in the operatory environment. The electronic display 12 may include a television, monitor, terminal, or other means for providing audio and video to a patient or practitioner. The electronic display 12 may also be paired with a remote headset, viewing wear, and a remote control to provide convenient control to the patient or practitioner in the operatory environment.

The electronic display 12 is fixedly attached to a bottom portion 42 of the housing assembly 14 using a mounting bracket 62 and hardware. The bracket 62 allows the electronic display 12 to be located directly above the patient's head. The electronic display 12 is fixed in position on a horizontal axis respectively positioned above a patient's head for some intended benefits. First, the fixed position above the patient's head prevents the practitioner from needlessly bumping into or constantly adjusting the electronic display 12. Second, the fixed position of the electronic display 12 improves the performance and efficiency of the practitioner by allowing the intraoral lamp assembly 28 to move independently of the electronic display 12 thereby not requiring adjustment of both electronic display 12 and intraoral lamp assembly 28 at the same time. Lastly, the fixed position of the electronic display 12 minimizes the usage of space in the operatory environment.

The electronic display 12 is mounted along a horizontal axis parallel to the housing assembly 14 and within a second predetermined distance from the second surface area within the operatory environment. In one embodiment, the second predetermined distance is approximately less than seven and a half feet. Alternatively, the second predetermined distance is approximately four and a half feet. Of course, the second predetermined distance may be adjusted depending upon the height of the ceiling in the operatory environment and the height of the head rest of the operatory chair 50 above the floor area. It should be noted that the second predetermined distance may be less than the first predetermined distance.

When ambient room lighting levels are low due to a particular procedure, the one or more directional task lighting assemblies 32, 34 will provide practitioners with sufficient light to access necessary instruments and equipment. The one or more directional task lighting assemblies 32, 34 is attached to a bottom portion 42 of the housing assembly 14 to provide lighting to work surface areas used by a practitioner in the operatory environment. The one or more directional task lighting assemblies 32, 34 includes one or more downward directional LEDs or other light producing members or elements to provide light to specific surface areas in the operatory environment. The directional LEDs may be fixed in a position upon installation, preferably at a range of approximately 10 degree beams. Of course, the directional task lighting assemblies 32, 34 may be directed in a multitude of degree settings downwardly towards a specific work surface area. The one or more directional task lighting assemblies, in one embodiment, includes three directional LED bulbs, such as MR16 LED bulbs with 3 LED lights therein, to provide light to surrounding work surface areas in the operatory environment. In another embodiment, the one or more directional task lighting assemblies 32, 34 includes a triplex directional down lighting. In one embodiment, the task lighting assembly 32, 34 is located proximal to the electronic display and pointed downward towards the work surface areas of the operatory environment.

An additional optional feature of the invention includes a remote dimming panel (not shown) or controller for use with the track lighting system 10. The track lighting system 10 would control all lighting options (intraoral illumination, ambient lighting, and directional task lighting) and the electronic display 12 as well as adjustment of lighting levels through the remote dimming panel or controller located proximal to the practitioner. The remote dimming panel may be programmed to enable the practitioner to adjust lighting levels in response to the needs of any given procedure, which is especially important during sedation dentistry. The dimming feature enables track light system to meet the maximum lighting requirements of multiple operatory sizes.

Alternatively, the various lighting options may be controlled individually. In one embodiment, the ambient lighting assembly 22, 24, 26, 28 may be turned on/off by a light switch located in the operatory environment. The directional task lighting assembly may be moved into a prefixed position and then turned on/off by a light switch located in the operatory environment. The intraoral lighting assembly 28 may have an on/off switch located on the intraoral assembly 28. The electronic display 12 may be manipulated by a remote control.

In operation, the track lighting system 10 and the electronic display 12 is more conveniently and efficiently controlled by the practitioner or patient in the operatory environment since all of the lighting options (intraoral illumination, ambient lighting, and directional task lighting) and electronic display 12 are convenient to the practitioner and/or patient in a single track lighting system 10.

Figure 13:
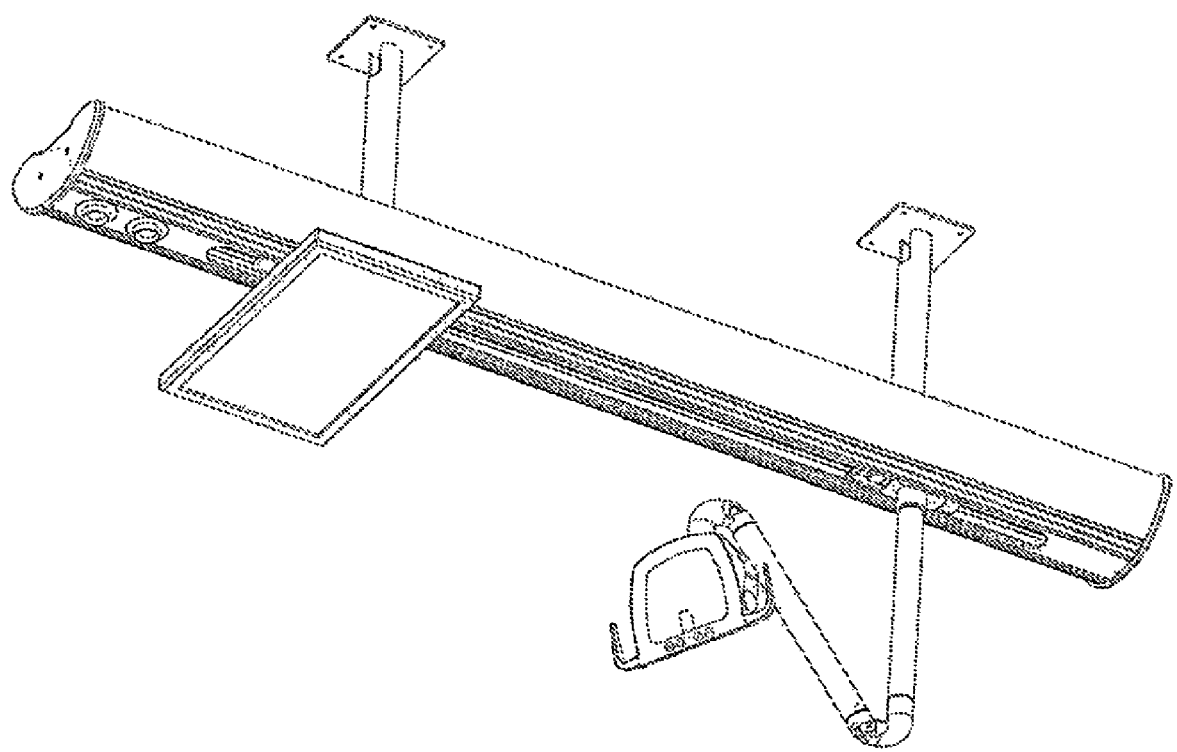
FIG. 13 illustrates an exemplary pendant mounted track lighting system.
Figure 14A:
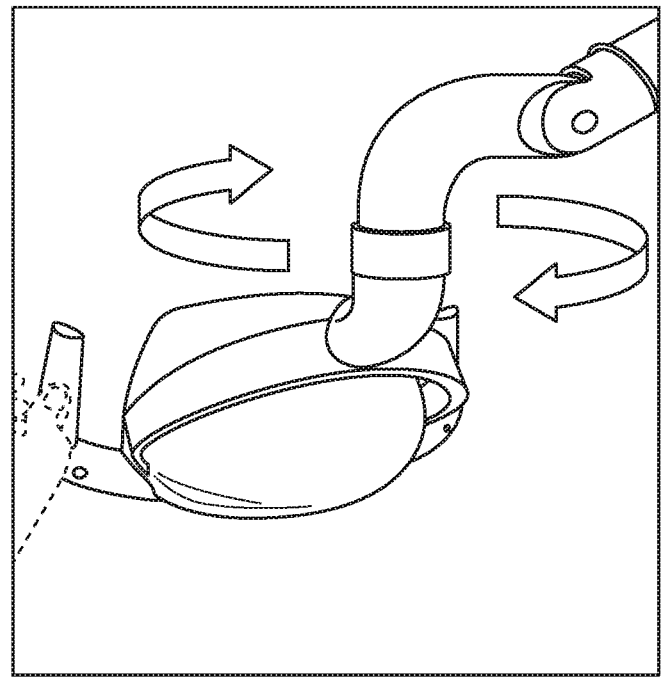
FIG. 14A illustrates a first light head rotation.
Figure 14B:
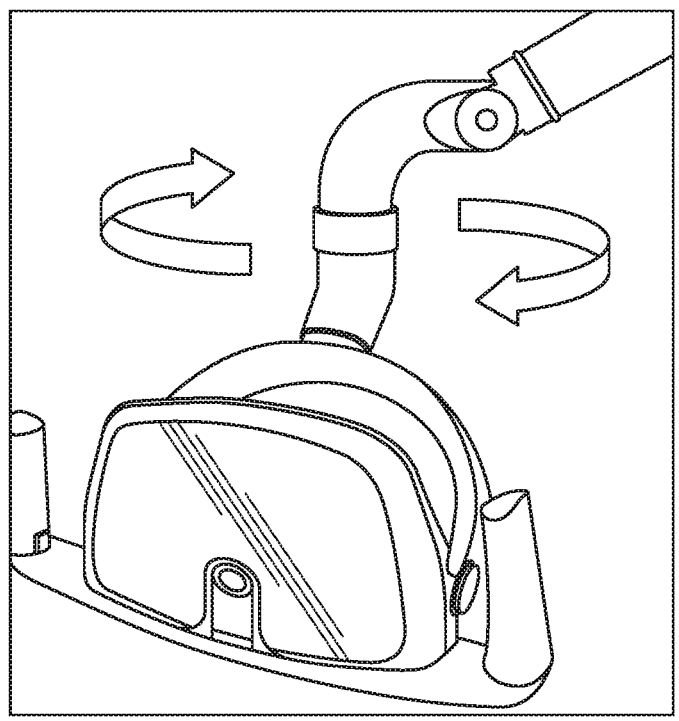
FIG. 14B illustrates a second light head rotation.

Referring to FIG. 13, an exemplary pendant mounted track lighting system 100 includes a light shield 110 having two end caps 120, 130. The light shield 110 is typically suspended by a pair of pendants 140, 150 attached to a respective pendant plates 160, 170. In the configuration illustrated, a flat panel light 180 is configured to slide on a track 190. In addition, a track light trolley 200 is configured to slide within the track 190. A light head 210, also referred to as an intra-oral light, is attached to the track light trolley 200 by a suspension tube 220. The suspension tube 220 includes a joint 230 enabling movement of the light head 210 in two dimensions and a swivel joint 240 enabling the light head 210 to rotate 360 degrees. FIG. 14A and FIG. 14B further illustrate the 360 degree rotation of the light head 210 around the swivel joint 240.

Figure 15A:
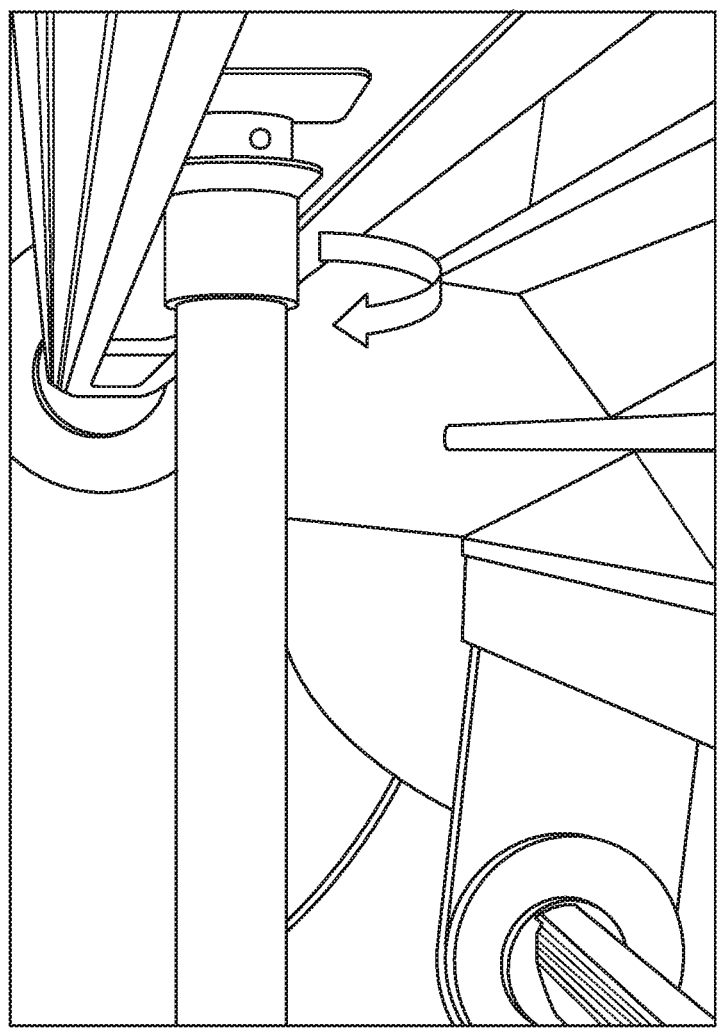
FIG. 15A illustrates an exemplary trolley collar.
Figure 15B:
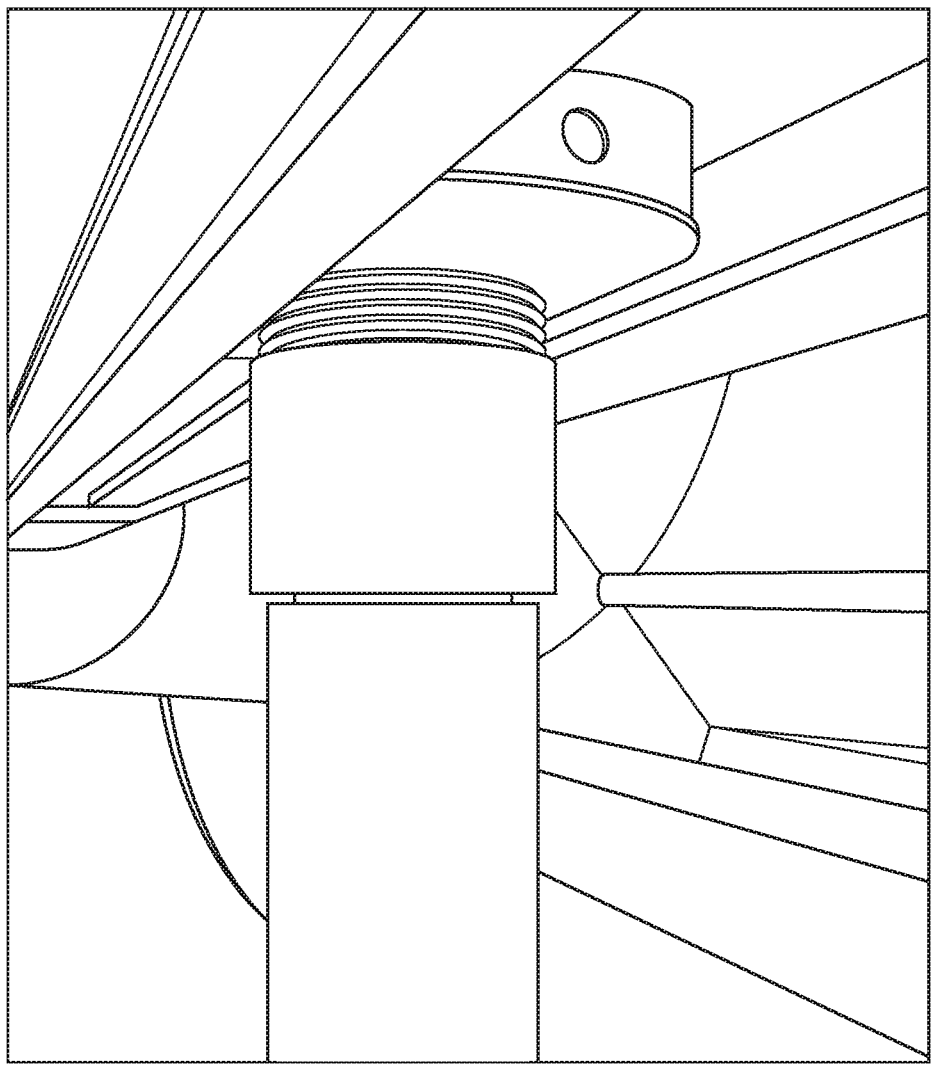
FIG. 15B illustrates the exemplary trolley collar.
Figure 15C:
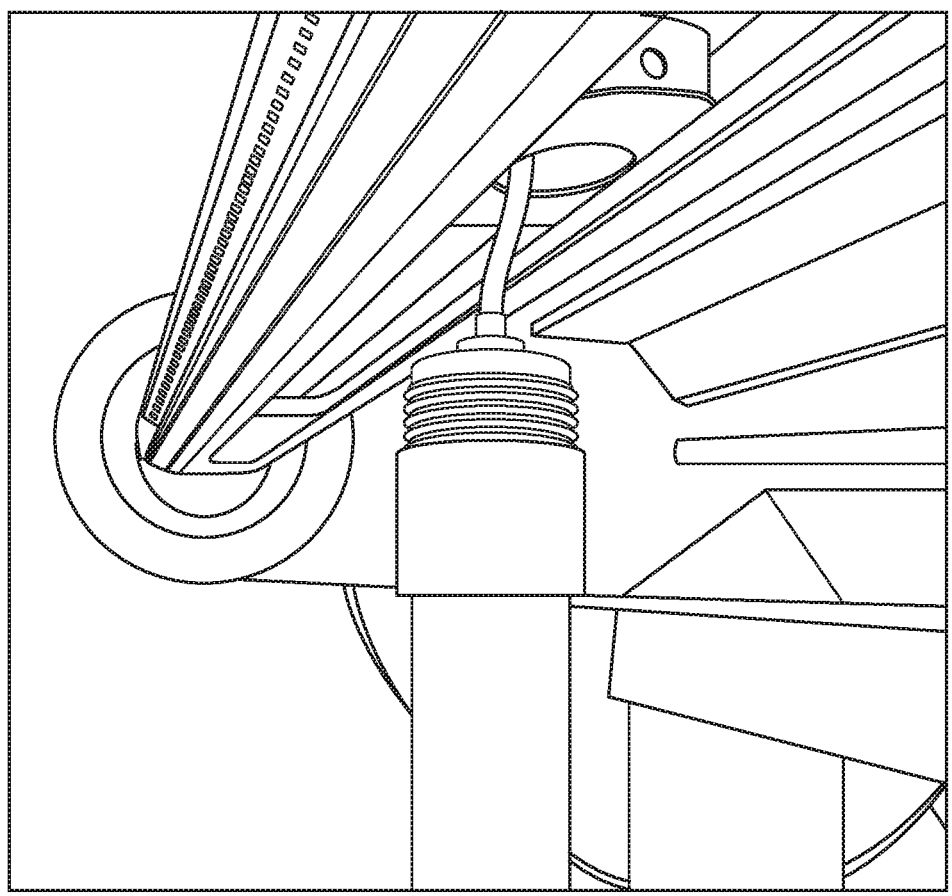
FIG. 15C illustrates the exemplary trolley collar.

Referring now to FIG. 15A, the suspension tube 220 may be linked a trolley 290 within the track 190 by a trolley collar 300. In one embodiment, the trolley collar 300 is designed to be threaded into the trolley 290. Turning the trolley collar 300 clockwise unscrews the trolley collar 300 from the track 190 for ease of light replacement in the light head 210. FIG. 15B illustrates a continued turning of the trolley collar 300 and FIG. 15B illustrates a separation of the trolley collar 300 from the track 190. Once the trolley collar 300 is separated from the 290 trolley 290, disconnection of a molex plug 310 enables the suspension tube 220 to be separated from the track 190 and thus provide easy bulb replacement in the light head 210. Thus, the trolley collar 300 enables quick change out of an intra-oral light should failure occur.

Figure 16A:
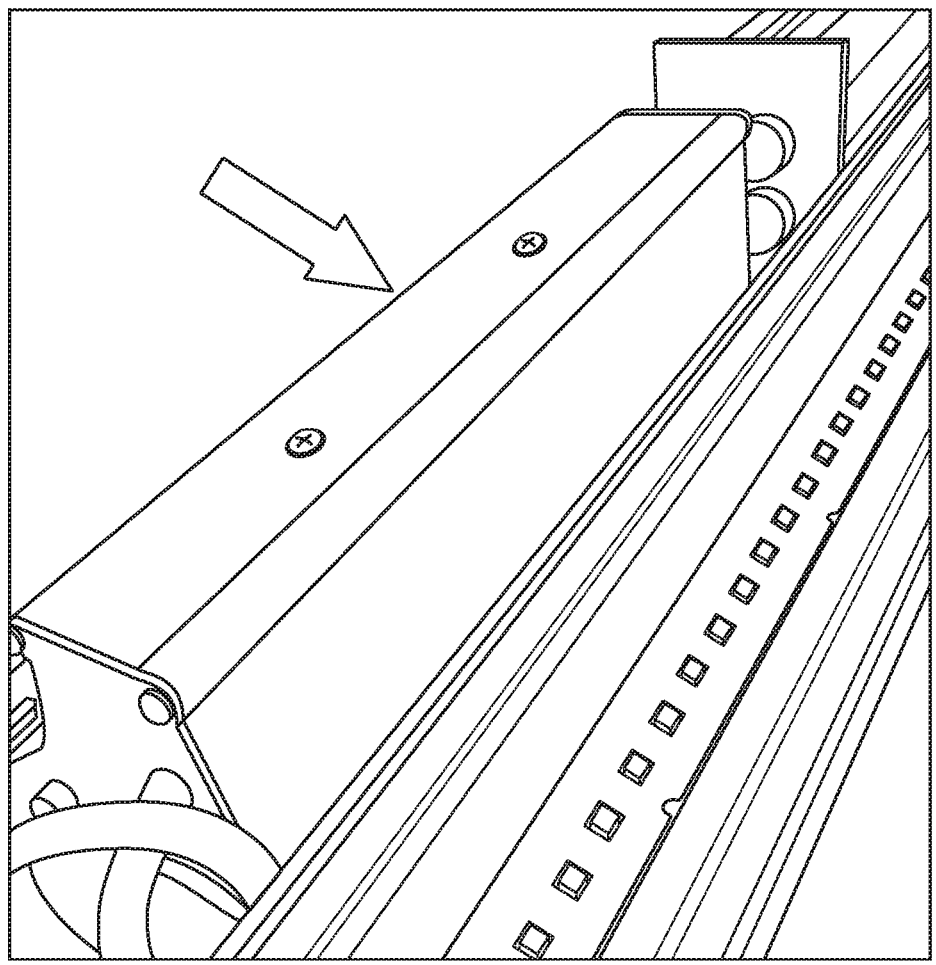
FIG. 16A illustrates wireless dimming capabilities.
Figure 16B:
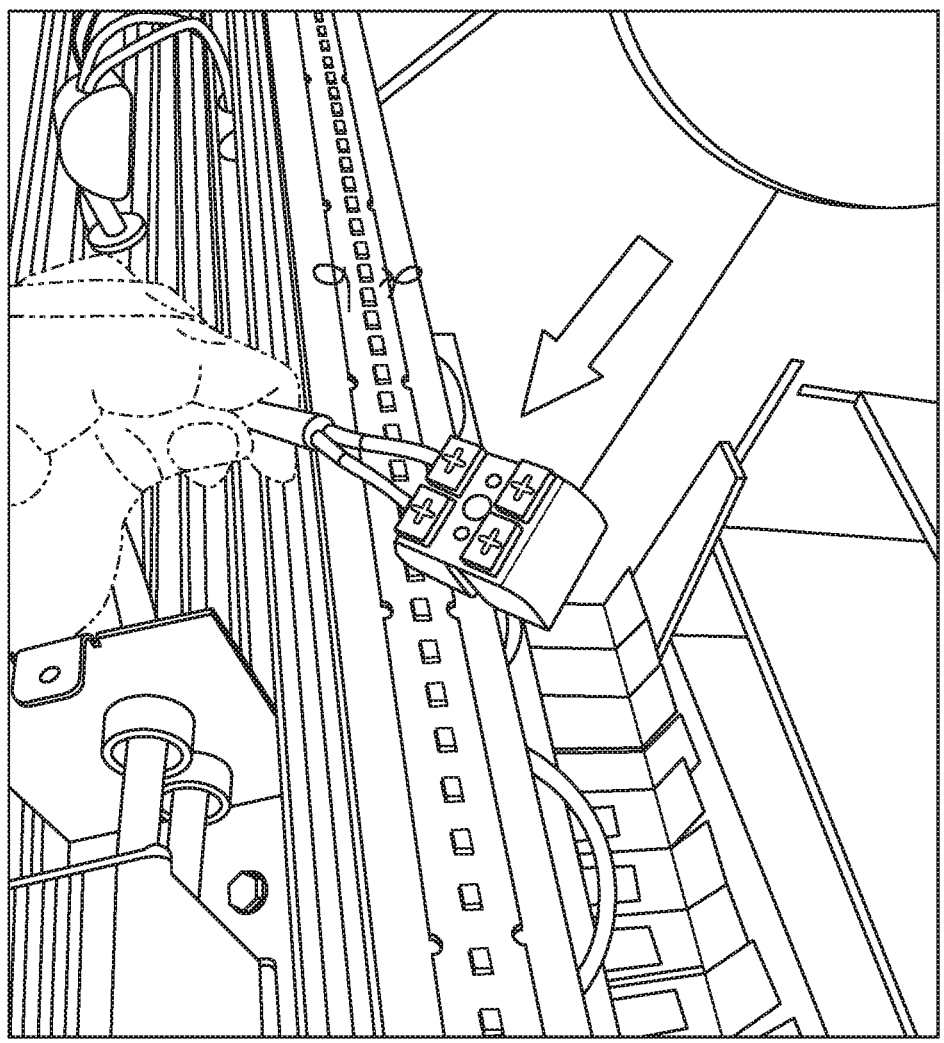
FIG. 16B illustrates wireless dimming capabilities.

FIG. 16A and FIG. 16B illustrate wireless dimming capabilities to reduce need for wiring. More specifically, there is a terminal block on the light to enable a connection of a commercially available 0-10 volt wireless dimmer.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A pendant mounted track lighting system comprising:
 a housing assembly having a top, side, middle, and bottom portions;
 a pair of hollow, tubular, elongated members having a top and a bottom end, the top portion of the housing assembly attached to the bottom end of the elongated members, the top end of the one or more elongated members having a brackets configured and arrange to mount to an overhead surface area;
 one or more ambient lighting assemblies attached to side portions and top portion of the housing assembly to provide general lighting, each ambient lighting assembly including an ambient housing and one or more fluorescent bulbs;
 a horizontal tracking rail suspended attached to a bottom portion of the housing assembly, the tracking rail extending along a portion of the housing assembly;
 a carriage mechanism slidably engaging the tracking rail;

an intra-oral light assembly connected to the carriage mechanism, the intra-oral light assembly having an articulating arm enabling 360 degree rotation to an intra-oral lamp; and an electronic display mounted to the bottom portion of the housing assembly, the electronic display fixed in position on a horizontal axis respectively positioned above a patient's head, the electronic display configured for a patient's visual and audio stimulation.

2. The pendant mounted track lighting system of claim 1 wherein the articulating arm comprises a swivel joint.

3. The pendant mounted track lighting system of claim 2 wherein the articulating arm further comprises a joint providing two dimensions of movement.

4. The pendant mounted track lighting system of claim 1 wherein the intra-oral lamp includes one or more lighting fixtures.

5. The pendant mounted track lighting system of claim 4 wherein the one or more lighting fixtures are light-emitting diode (LED) lighting.

6. A pendant mounted track lighting system comprising:

a housing assembly having a top, side, middle, and bottom portions;

a pair of hollow, tubular, elongated members having a top and a bottom end, the top portion of the housing assembly attached to the bottom end of the elongated members, the top end of the one or more elongated members having a brackets configured and arrange to mount to an overhead surface area;

one or more ambient lighting assemblies attached to side portions and top portion of the housing assembly to provide general lighting, each ambient lighting assembly including an ambient housing and one or more fluorescent bulbs;

a horizontal tracking rail suspended attached to a bottom portion of the housing assembly, the tracking rail extending along a portion of the housing assembly;

a carriage mechanism slidably engaging the tracking rail;

an intra-oral light assembly releasably connected to the carriage mechanism by a trolley collar; and an electronic display mounted to the bottom portion of the housing assembly, the electronic display fixed in position on a horizontal axis respectively positioned above a patient's head, the electronic display configured for a patient's visual and audio stimulation.

7. The pendant mounted track lighting system of claim 6 wherein the trolley collar is threaded to the carriage mechanism.

8. The pendant mounted track lighting system of claim 7 wherein the trolley collar includes an internal molex plug.

* * * * *